United States Patent [19]

Powers et al.

[11] 4,253,452

[45] Mar. 3, 1981

[54] EAR PLUG ASSEMBLY

[75] Inventors: William R. Powers, Penns Grove, N.J.; William H. Lotter, Jr., Newark, Del.

[73] Assignee: Specialty Composites Corporation, Newark, Del.

[21] Appl. No.: 42,092

[22] Filed: May 24, 1979

[51] Int. Cl.³ ............................................. A61F 11/00
[52] U.S. Cl. ....................................... 128/152; 264/230; 264/249; 156/293; 29/447; D24/67; 128/285
[58] Field of Search .............. 128/152, 151, 206.11, 128/285; 264/230, 249; 156/293, 294; 29/447; D24/67

[56] References Cited

U.S. PATENT DOCUMENTS

| | | | |
|---|---|---|---|
| Re. 29,487 | 12/1977 | Gardner, Jr. .................... | 128/152 |
| D. 241,881 | 10/1976 | Peterson et al. ................ | D24/67 |
| 3,130,260 | 4/1964 | Gray ................................ | 264/230 X |
| 3,758,916 | 9/1973 | Wetmore ......................... | 29/447 X |
| 3,983,875 | 10/1976 | Truman ........................... | 128/285 |

FOREIGN PATENT DOCUMENTS

| | | | |
|---|---|---|---|
| 2325823 | 12/1974 | Fed. Rep. of Germany ........... | 128/152 |
| 74535 | 12/1960 | France ..................................... | 128/151 |

*Primary Examiner*—Henry J. Recla
*Attorney, Agent, or Firm*—Connolly and Hutz

[57] ABSTRACT

An ear plug assembly includes a pair of plug bodies made from open cell resilient foam material having a slow recovery rate which are interconnected by a flexible cord having its free ends inserted into preformed holes in the plug bodies before the holes close under the influence of the recovery rate.

7 Claims, 5 Drawing Figures

U.S. Patent        Mar. 3, 1981        4,253,452
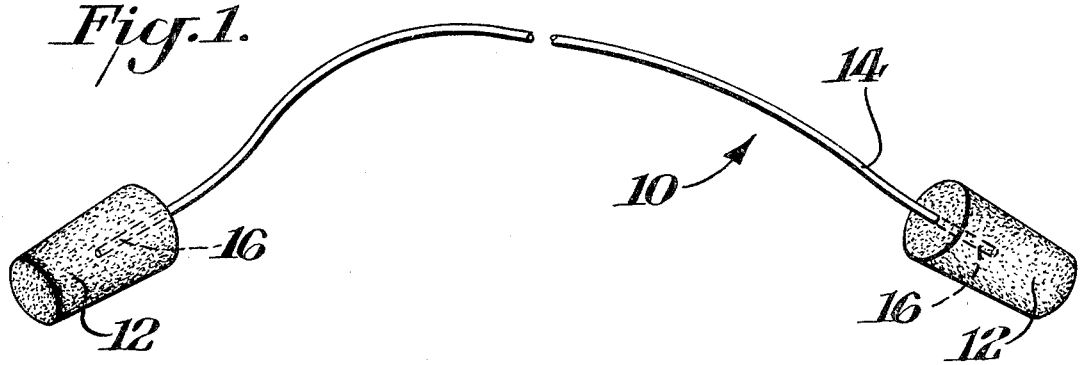
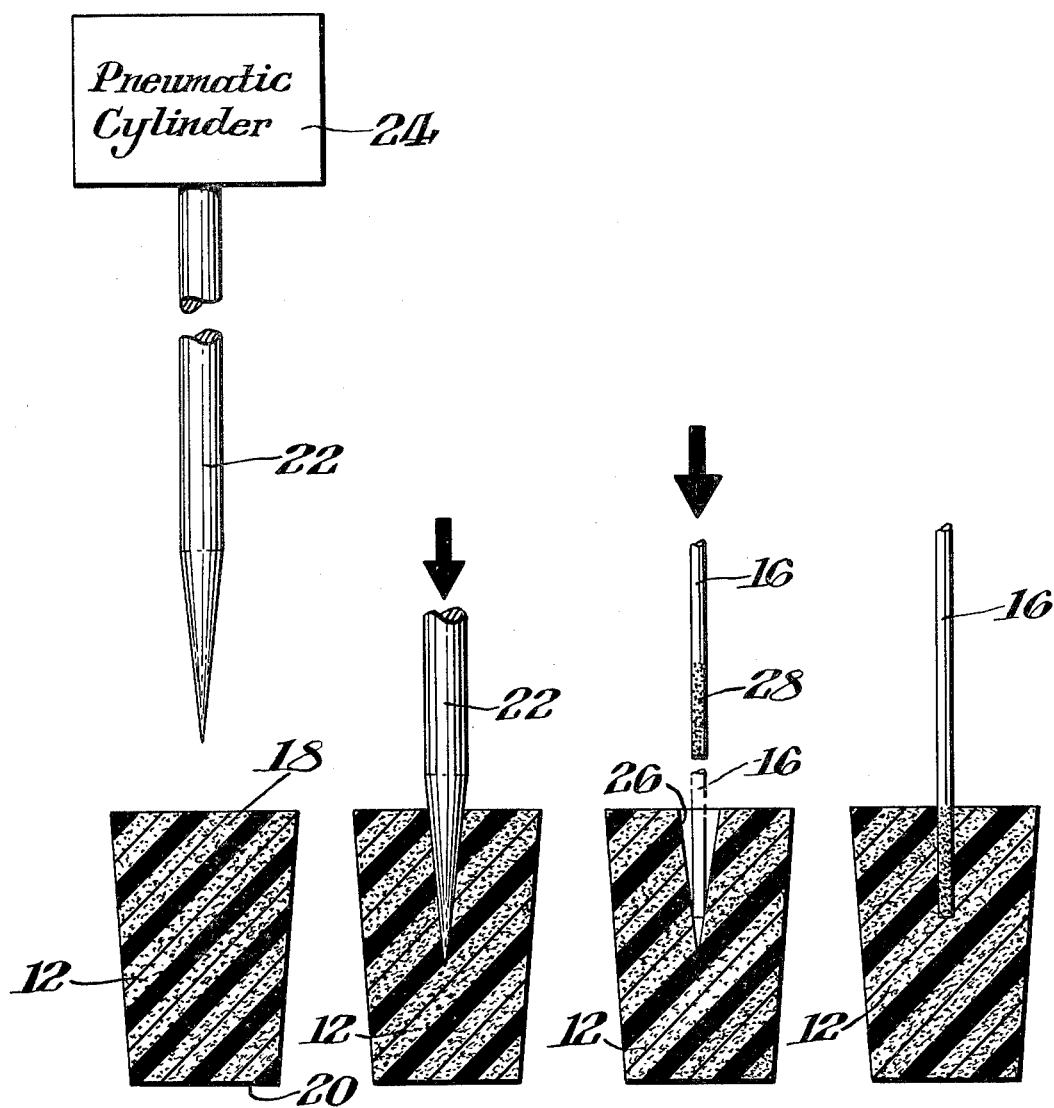
Fig.2.    Fig.3.    Fig.4.    Fig.5.

EAR PLUG ASSEMBLY

BACKGROUND OF INVENTION

Ear plugs are widely used devices for hearing protection. However, they have the disadvantage of being small and easily lost. This is highly objectionable in some areas of use, for example, in the food processing industry where the presence of a "lost" ear plug in a food product causes great consternation and trauma.

To reduce the chance of an ear plug becoming lost it is common to fasten two plugs together by means of a cord of sufficient length to permit the user to conveniently insert both plugs in his ears. Various methods are used to fasten cords to plugs depending upon the materials involved. One widely used ear plug, a polyvinyl chloride foam product has the cord welded to the plug by means of a thermal "spot weld".

Prior art arrangements generally related to the field of this invention include U.S. Pat. No. 2,538,339, RE No. 29,487, DES No. 245,202 and German Offenlegungsschrift No. 23 25 823.

SUMMARY OF INVENTION

It is an object of this invention to provide an improved method of manufacturing corded foam ear plugs.

The further object is to provide corded foam ear plugs having the cord attached at the optimum position to give maximum functional strength and aesthetic functional acceptance.

The invention is based on the surprising observation that slow recovery foams exhibit "memory". Thus, if a foam plug is penetrated by a sharp pointed needle, i.e. a bodkin, which after a period of time is withdrawn, there remains a hole which closes at a rate dependent upon the length of time the bodkin remained in the foam. The invention takes advantage of this characteristic by providing such holes in a pair of plug bodies and inserting the free ends of a cord therein before the holes close.

To further maximize the securement of the free ends of the cord in the plug bodies a suitable bonding agent may be provided on the free ends and/or in the hole before the hole closes and the free end in inserted. The plug bodies may take any suitable form which is generally cylindrical or variations thereof such as frusto-conical.

THE DRAWINGS

FIG. 1 is a perspective view of the ear plug assembly in accordance with this invention; and FIGS. 2-5 are schematic views in cross section showing the steps of forming the assembly illustrated in FIG. 1.

DETAILED DESCRIPTION

As indicated in FIG. 1 ear plug assembly 10 includes a pair of plug bodies 12, 12 interconnected by a flexible cord 14 of a length sufficient to extend from one ear of the user to the other. As illustrated therein the free ends 16, 16 of cord 14 are inserted into plug bodies 12, 12 in the manner later described. Bodies 12, 12 may be of any suitable form such as cylindrical, frusto-conical or other conventional shapes. These shapes are generically referred to hereafter as "generally cylindrical".

FIGS. 2-5 illustrate the steps for forming ear plug assembly 10. As illustrated therein plug body 12 is made from an open cell resilient foam material having a low recovery rate. Suitable slow recovery polymer foams include PVC ear plugs marketed by EAR Corporation, slow recovery polyurethane foam by the Edmont-Wilson Company under the name Temper Foam and polyurethane foam manufactured by Specialty Composites and marketed by Norton Company. After the plug body 12 has been cut or otherwise formed in the proper size and shape such as the slightly frusto-conical shape illustrated in FIGS. 2-5, a piercing tool such as a sharp pointed needle or bodkin is thrust axially into the center of the larger end face 18 remote from smaller end face 20. In one practice of the invention the bodkin is a one-eighth inch diameter steel rod tapered to a sharp point over a taper length of about five-eighth inch. Bodkin 22 is thrust at high velocity by means, for example, of pneumatic cylinder 24 to a depth of about one-half inch (FIG. 3). Bodkin 22 is permitted to remain inserted in the thus formed hole 26 for a sufficient period of time to permit the foam material around hole 26 to distort. It has been found that an optimum dwell time of bodkin 22 in plug body 12 is about two to four seconds for the illustrated arrangement. In this respect, a shorter dwell time results in holes closing too rapidly while longer periods produce holes which close too slowly for optimum production rates.

After bodkin 22 is removed, free end 26 of cord 14 is inserted into preformed hole 26 (FIG. 4). Any suitable material may be used for flexible cord 14. It is preferred, however, to use a very limp 0.03 to 0.04 inch diameter PVC cord. Next, as illustrated in FIG. 5, the material around hole 26 is permitted to close under the influence of the recovery rate to surround and intimately contact free end 16 and thereby secure each free end in its plug body. A characteristic of the foam material is that upon distortion by the application of a force thereto the foam material temporarily remains distorted and then slowly recovers its original shape. The inherent degree of resiliency of this material in connection with its tendency to recover to its original shape offers an effective manner of assembling the free ends 16, 16 of cord 14 into the plug bodies 12, 12.

To further assure an effective securement of free ends 16, 16 into plug bodies 12, 12, each free end 16, 16 is covered with a suitable bonding agent 28. Preferably the bonding agent is a thermoplastic although any of a wide range of adhesives can be used. The action of the recovery of foam body 12 to close hole 26 operates in cooperation with bonding agent 28 to thereby result in an attachment of cord 14 to the plug bodies with maximum functional strength.

It is possible to practice the concepts of this invention by variations from the above-described process particularly with regard to the indicated parameters. Thus one skilled in the art may determine such variations by evaluating different foam materials than the polyurethane referred to above with different penetration and dwell times carried out, for example, at work-room temperature. Other slow recovery foams may exhibit a hole closure time (to a diameter of one-sixteenth inch) of three to six seconds with a bodkin dwell time of three to five seconds. This range of dwell time, when considered with the above indicated range of two to four seconds, thus results in a broader range of two to five seconds. It is to be understood, however, that foams requiring longer dwell times can be used within the concepts of this invention but at some sacrifice of manufacturing costs.

As can be appreciated, the ear plug assembly of this invention is the result of techniques which lend themselves to optimum production rates while providing maximum functional strength and at the same time aesthetic functional acceptance. Thus, for example, plug bodies 12, 12 and cord 14 may be made of brightly colored materials or may be of any suitable shape or color as to enhance its aesthetic appeal.

What is claimed is:

1. An ear plug assembly comprising a pair of generally cylindrical plug body means adapted to be inserted into the ear canal of an individual, each of said plug body means being made from an open cell resilient foam material having a slow recovery rate, a flexible cord of a length at least sufficient to extend from one ear of the user to the other ear and having a pair of free ends, and each said free ends of said cord being secured into a respective one of said plug body means by the method comprising the steps of inserting a piercing tool into said plug body means made from said open cell resilient foam material having a slow recovery rate, maintaining the piercing tool in said plug body means for a sufficient period of time to distort the body thereat and temporarily create a hole corresponding to the piercing tool, withdrawing the piercing tool to expose the hole, inserting a free end of said elongated flexible cord into the exposed hole, permitting the hole to close upon the free end of the cord, and repeating the step with the second plug body means and the opposite free end of the cord.

2. The ear plug assembly of claim 1 wherein the method includes the step of applying a bonding agent to each of the free ends of the cord before the free ends are inserted in the holes.

3. The earplug assembly of claim 2 wherein the method includes the step of maintaining the piercing tool in each plug body for a dwell time of about two to five seconds.

4. The earplug assembly of claim 3 wherein the method includes the step of maintaining the piercing tool in each said plug body means for a dwell time of about two to four seconds.

5. The earplug assembly of claim 4 wherein the plug body means are made of polyurethane, and the method further includes the step of inserting the piercing tool to a depth of about 0.5 inches in each plug body means, and each free end having a diameter of about 0.03 to 0.04 inches.

6. The earplug assembly of claim 5 wherein each plug body means is slightly frusto-conically shaped with a large end face and a smaller end face opposite therefrom, and each free end of the cord is inserted longitudinally into its plug body means through its large end face thereof.

7. The earplug of claim 1 wherein the method further includes the step of maintaining the piercing tool in each plug body means for a dwell time of about two to five seconds.

* * * * *